United States Patent
Martinez et al.

(10) Patent No.: US 12,383,569 B2
(45) Date of Patent: Aug. 12, 2025

(54) IMMUNOMODULATORY OLIGOSACCHARIDES FOR THE TREATMENT OF PAIN

(71) Applicant: Intrinsic Medicine, Inc., Des Moines, WA (US)

(72) Inventors: Alexander Martinez, Des Moines, WA (US); Jason Ferrone, Fallbrook, CA (US)

(73) Assignee: Intrinsic Medicine, Inc., Seattle, WA (US)

( * ) Notice: Subject to any disclaimer, the term of this patent is extended or adjusted under 35 U.S.C. 154(b) by 802 days.

(21) Appl. No.: 17/606,149

(22) PCT Filed: Mar. 25, 2020

(86) PCT No.: PCT/US2020/024621
§ 371 (c)(1),
(2) Date: Oct. 25, 2021

(87) PCT Pub. No.: WO2020/210027
PCT Pub. Date: Oct. 15, 2020

(65) Prior Publication Data
US 2022/0193099 A1    Jun. 23, 2022

Related U.S. Application Data

(60) Provisional application No. 62/931,386, filed on Nov. 6, 2019, provisional application No. 62/831,245, filed on Apr. 9, 2019.

(51) Int. Cl.
*A61K 31/702* (2006.01)
(52) U.S. Cl.
CPC .................. *A61K 31/702* (2013.01)
(58) Field of Classification Search
None
See application file for complete search history.

(56) References Cited

U.S. PATENT DOCUMENTS

| | | |
|---|---|---|
| 9,034,847 B2 | 5/2015 | Morrow et al. |
| 10,098,903 B2 | 10/2018 | Morrow et al. |
| 11,058,697 B2 | 7/2021 | Morrow et al. |
| 11,234,992 B2 | 2/2022 | Gordts et al. |
| 2011/0257222 A1 | 10/2011 | Sucholeiki |
| 2019/0030054 A1 | 1/2019 | Yang et al. |
| 2020/0230161 A1 | 7/2020 | Bode et al. |
| 2020/0237793 A1 | 7/2020 | Bode et al. |
| 2021/0236526 A1 | 8/2021 | Bode et al. |
| 2021/0236527 A1 | 8/2021 | Bode et al. |
| 2021/0283155 A1 | 9/2021 | Morrow et al. |

FOREIGN PATENT DOCUMENTS

| | | |
|---|---|---|
| EP | 2465509 A1 | 6/2012 |
| WO | 2017190755 A1 | 11/2017 |
| WO | 2019071021 A2 | 4/2019 |
| WO | 2019111115 A2 | 6/2019 |
| WO | 2019121929 A1 | 6/2019 |
| WO | 2019123316 A1 | 6/2019 |

OTHER PUBLICATIONS

Cho, C et al., "3'-Siallylactose Promotes Cartilage Regeneration By Extracellular Matrix Remodeling", Osteoarthritis and Cartilage, Abstract 273, Retrieved from the Internet: URL:https://sdfestaticassets-eu-west-1.sciencedirectassets.com/shared-assets/67/images/lpx.png?fr=cpcnjs [retrieved on Dec. 8, 2022], Apr. 16, 2018, S144.

Kang, L-J. et al., "3'-Sialyllactose as an inhibitor of p65 phosphorylation ameliorates the progression of experimental rheumatoid arthritis", British Journal of Pharmacology, 175(23), DOI: 10.1111/BPH.14486, Oct. 17, 2018, 4295-4309.

Kim, D. et al., "3'-Sialyllactose Inhibits Inflammatory Response In Experimental Arthritis Model", DOI: 10.1016/j.joca.2018.02.281 Retrieved from the Internet: URL:https://www.oarsijournal.com/action/showPdf?pii=S1063-4584(18)30381-9 [retrieved on Oct. 13, 2020] (Abstract), Apr. 30, 2018, 1 pg.

Aranda-Villalobos, P. et al., "Normalization of Widespread Pressure Pain Hypersensitivity 26, 28/26-27, After Total Hip Replacement in Patients With Hip Osteoarthritis Is Associated With Clinical and 29/28/26-27 Functional Improvements", Arthritis & Rheumatism vol. 65, No. 5, 2013, 1262-1270.

De Martino, M. et al., "Working Towards an Appropriate Use of Ibuprofen in Children: An Evidence-Based Appraisal", Drugs 77, 2017, 1295-1311.

Henriet, P. et al., "Review: Are matrix metalloproteinases and their inhibitors reliable diagnosis biomarkers and attractive therapeutic targets in endometriosis?", Dovepress vol. 2016:3, 2016, 81-92.

Waldron, A. L. et al., "Oxidative stress-dependent MMP-13 activity underlies glucose neurotoxicity", Journal of Diabetes Complications 32(3), 2018, 249-257.

*Primary Examiner* — Patrick T Lewis
(74) *Attorney, Agent, or Firm* — Carolyn S. Elmore; Mahreen Chaudhry Hoda; Elmore Patent Law Group, P.C.

(57) ABSTRACT

The disclosure provides for methods of treating pain and neuroinflammatory pain conditions with certain oligosaccharides.

19 Claims, 6 Drawing Sheets

IMMUNOMODULATORY OLIGOSACCHARIDES FOR THE TREATMENT OF PAIN

RELATED APPLICATIONS

This application is a US National stage entry of International Application No. PCT/US20/24621, which designated the United States and was filed on Mar. 25, 2020, published in English, which claims the benefit of U.S. Provisional No. 62/831,245, filed Apr. 9, 2019 and U.S. Provisional No. 62/931,386, filed Nov. 6, 2019. The entire teachings of the above applications are incorporated herein by reference.

TECHNICAL FIELD

The disclosure provides for immunomodulatory oligosaccharides, and therapeutic uses thereof for the treatment of pain.

BACKGROUND

Neuropathic pain is a recognized type of pathological pain where nociceptive responses persist beyond the resolution of damage to the nerve or its surrounding tissue. Very often, neuropathic pain is disproportionately enhanced in intensity (hyperalgesia) or altered in modality (hyperpathia or allodynia) in relation to the stimuli. Animal models of neuropathic pain based on various types of nerve injuries (peripheral versus spinal nerve, ligation versus chronic constrictive injury) have persistently implicated a pivotal role for TNF-α at both peripheral and central levels of sensitization. Despite a lack of success in clinical trials of anti-TNF-α therapy in alleviating the sciatic type of neuropathic pain, the intricate link of TNF-α with other neuro-inflammatory signaling systems (e.g., chemokines and p38 MAPK) is an area in which no safe and effective therapies exist.

Neuropathic pain is characterized by disproportionate hypersensitivity to stimuli (hyperalgesia), abnormal pins and-needles or electric-shock-like sensations (hyperpathia) and, finally, nociceptive responses to non-noxious stimuli (allodynia). It has been discovered that inflammation and macrophage phenotype play a part in the pathophysiology of persistent and chronic pain conditions and syndromes. Therefore, an unmedical need exists for safe and effective immunomodulatory therapies that have the ability to ameliorate the symptoms of persistent and chronic pain.

SUMMARY

Chronic macrophage inflammation plays a key role in the development and progression of persistent, chronic pain. The data presented herein, indicate that 3'-sialyllactose (3'SL) and 6'-sialyllactose (6'SL) based oligosaccharides and purified preparations comprising or consisting of 3' SL and/or 6' SL attenuate macrophage inflammation and suppress the secretion of pro-inflammatory cytokines, like interleukin (IL)-1beta and IL-6. The efficacy profile, combined with the proven safety of these compounds in non-clinical studies, provides a potential benefit for several pain disorders.

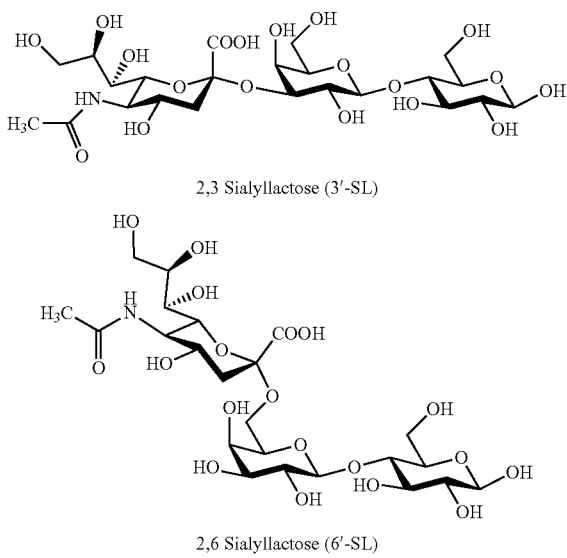

2,3 Sialyllactose (3'-SL)

2,6 Sialyllactose (6'-SL)

In a particular embodiment, the disclosure provides a method for treating a subject having or suspected of having pain with an inflammatory component, comprising administering to the subject an effective amount of an oligosaccharide, or a pharmaceutical composition comprising the oligosaccharide, wherein the oligosaccharide comprises a structure of Formula I, I(a) or II:

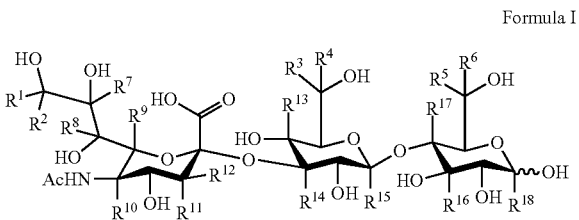

Formula I

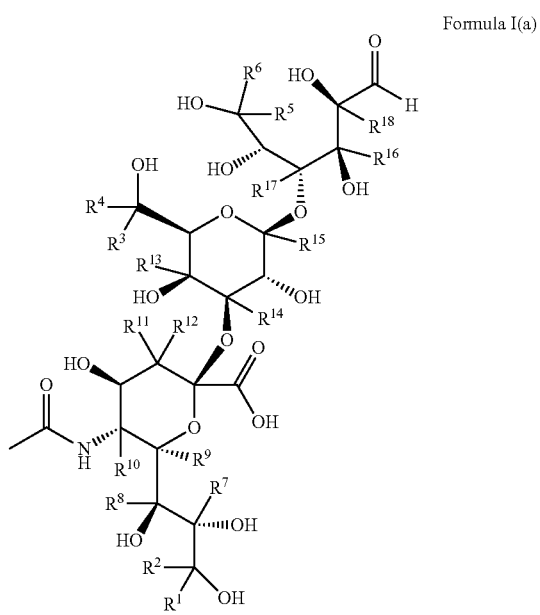

Formula I(a)

-continued

Formula II

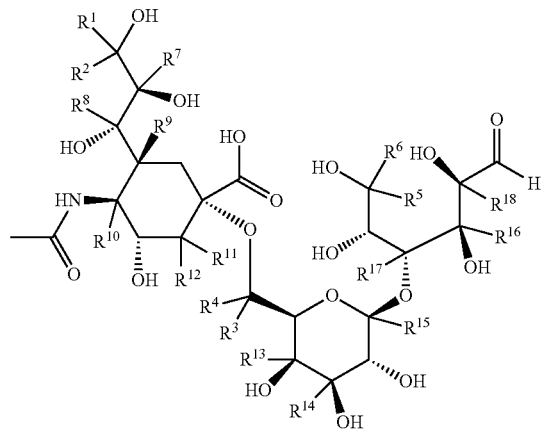

or a pharmaceutically acceptable salt, solvate, or prodrug thereof, wherein, $R^1$-$R^{18}$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$) cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a ($C_1$-$C_5$)alkyl; and R' is independently selected from H, D, an unsubstituted or substituted ($C_1$-$C_6$) alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, and an unsubstituted or substituted aryl.

In another embodiment, the disclosure also provides a method for treating a subject suffering from a persistent or chronic pain, comprising administering to the subject an effective amount of an oligosaccharide, or a pharmaceutical composition comprising the oligosaccharide, wherein the oligosaccharide comprises a structure of Formula I(b) or I(c):

Formula I(b)

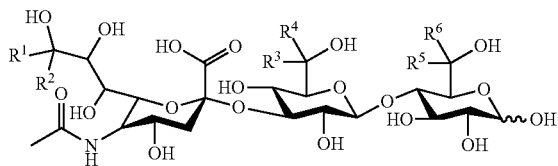

Formula I(c)

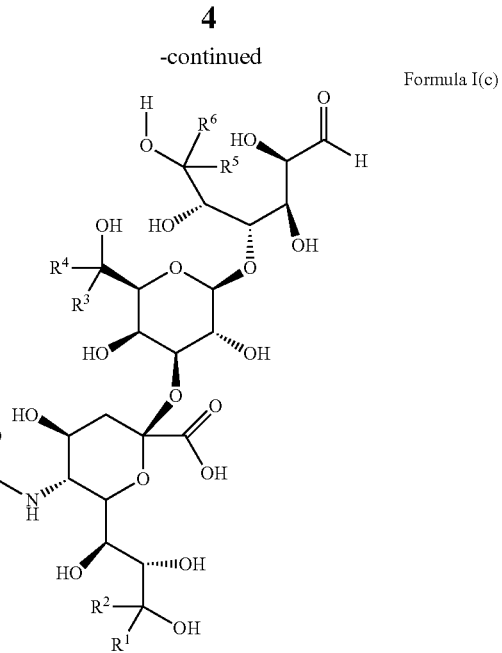

or a pharmaceutically acceptable salt, solvate, or prodrug thereof, wherein, $R^1$-$R^6$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$) cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a ($C_1$-$C_5$)alkyl; and R' is independently selected from H, D, an unsubstituted or substituted ($C_1$-$C_6$) alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, and an unsubstituted or substituted aryl.

In yet another embodiment, the disclosure further provides a method for treating a subject having persistent or chronic pain, comprising administering to the subject an effective amount of an oligosaccharide, or a pharmaceutical composition comprising the oligosaccharide, wherein the oligosaccharide comprises a structure of Formula I(d), I(e) or II(a):

Formula I(d)

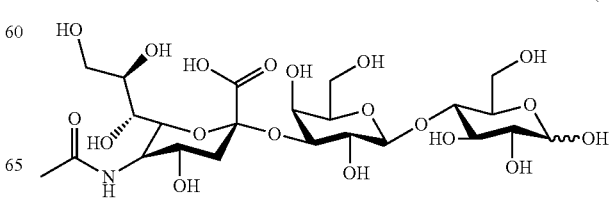

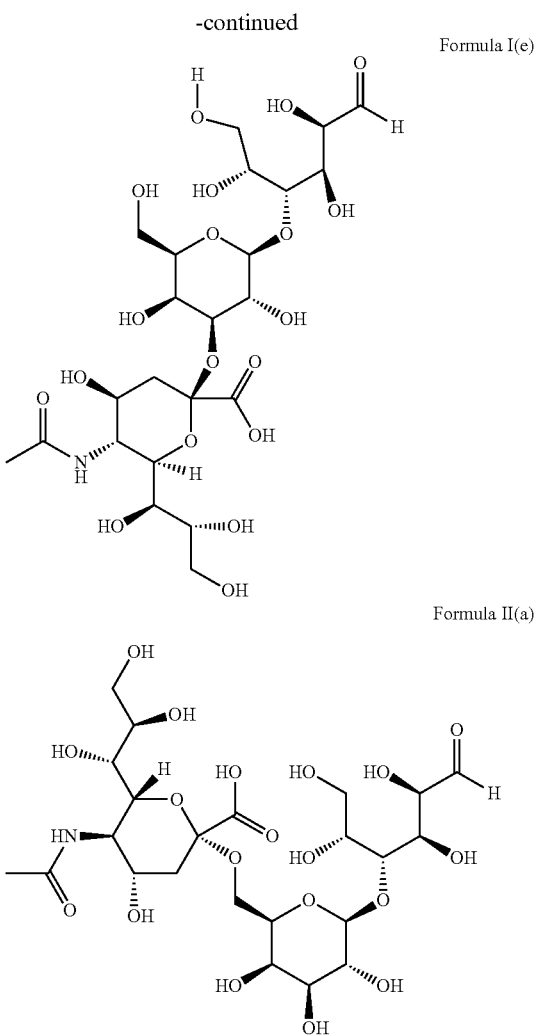

Formula I(e)

Formula II(a)

or a pharmaceutically acceptable salt, solvate, or prodrug thereof. In a certain embodiment, a method disclosed herein comprises orally administering an oligosaccharide of the disclosure or a pharmaceutical composition comprising an oligosaccharide of the disclosure to a subject. In yet a further embodiment, a method disclosed herein comprises orally administering to a subject a nutritional composition comprising at least one oligosaccharide of the disclosure.

In certain embodiments, the nutritional composition comprises or consists of 3'SL, 6'SL or a combination of 3'SL and 6'SL.

In other embodiments, the nutritional composition comprise or consists of 3'SL, 6' SL or a combination thereof at 145 mg/L or greater of 3'SL, 6'SL or a combination of 3'SL and 6' SL. In another embodiment, the nutritional composition comprises at least 9% (e.g., 10, 15, 20, 25, 30, 35, 40, 45, 50, 55, 60, 65, 70, 75, 80, 85, 90, 95, or 100%; or any value between any of the foregoing) 3'SL, 6'SL or a combination thereof of the total oligosaccharides in the composition. In another embodiment, a pharmaceutical composition comprising the oligosaccharide of the disclosure is formulated as a tablet or a capsule.

In other embodiments, the persistent and chronic pain may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain.

In yet another aspect a method of treating a patient with chronic or acute pain is provided, comprising administering to the patient a compound described herein. In one embodiment the pain is a nociceptive pain, a neuropathic pain and/or a dysfunctional pain. In another embodiment the pain is chronic nociceptive pain, chronic neuropathic pain and/or chronic dysfunctional pain. The pain may be (a) central neuropathic pain; (b) peripheral neuropathic pain; (c) nociceptive pain; (d) mixed pain syndromes; (e) dysfunctional pain; or (f) neuropathic, nociceptive or mixed headaches. Preferably, the pain is chronic central neuropathic pain; chronic peripheral neuropathic pain; or chronic nociceptive pain. According to the uses and the methods of the invention, the central neuropathic pain is preferably selected from the group consisting of multiple sclerosis pain, spinal cord injury pain (SCI; Paraplegia), Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.

According to the uses and the methods of the invention the peripheral neuropathic pain is preferably selected from the group consisting of brachialgia paraesthetica, carpal tunnel syndrome, erythromelalgia, facial neuralgia, postherpetic neuralgia, postoperative neuralgia, posttraumatic neuralgia, sciatica, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.

According to the uses and the methods of the invention the nociceptive pain is preferably selected from the group consisting of visceral pain; ischemic pain; Raynaud syndrome related pain; degenerative joint pain such as osteoarthritis pain or arthritic pain; rheumatic pain; tendinitis associated pain, such as epicondylitis, achillodynia, fasciitis pain, keel spur pain; frozen shoulder; arthritis; degenerative vertebral pain; degenerative cervical pain; inflammatory pain; myofascial pain syndrome; muscular trigger points and myalgia.

According to the uses and the methods of the invention the mixed pain syndrome is preferably selected from the group consisting of cervical syndrome, cancer pain, low back pain, abdominal pain, complex regional pain syndrome (CRPS, also referred to as algodystrophy, reflex dystrophy, Sudeck's atrophy), postamputation pain, anal pain, disc herniation and degeneration, degenerative spinal pain, failed back surgery syndrome (FBS) and acute and chronic post-surgical pain (CPSP).

According to the uses and the methods of the invention the dysfunctional pain is preferably selected from the group consisting of soft tissue rheumatism, fibromyalgia, chronic pelvic pain syndrome (CPPS), chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.

According to the uses and the methods of the invention the headache is preferably selected from the group consisting of cluster headache, migraine, tension type headache, hemicrania, trigeminal autonomic cephalalgia, SUNCT syndrome, nummular headache, occipital neuralgia and trigeminal neuralgia and neuropathy.

In one embodiment the compounds described herein according to the uses and the methods of the invention is to be administered topically or systemically, preferably topically, more preferably dermally. In a preferred embodiment the sialyllactose or a salt thereof is to be administered topically and the pain is a peripheral neuropathic pain, preferably a localized peripheral neuropathic pain, or the pain is a degenerative joint pain or tendinitis associated pain.

In another embodiment, the disclosure also provides a method for treating a subject having or suspected of having an inflammatory disease or an autoimmune disorder, comprising administering to the subject an effective amount of an oligosaccharide disclosed herein, or a pharmaceutical composition comprising the oligosaccharide disclosed herein, with another therapeutic agent.

In a further embodiment, the disclosure also provides a method for treating a subject having or suspected of having an inflammatory disease or an autoimmune disorder, comprising administering to the subject an effective amount of an oligosaccharide disclosed herein, or a pharmaceutical composition comprising the oligosaccharide disclosed herein, with a nonsteroidal anti-inflammatory drug, a glucocorticoid, a biologic response modifier or an opioid.

Examples of nonsteroidal anti-inflammatory drugs include, but are not limited to, Aminophenazone, Ampyrone, Azapropazone, Clofezone, Difenamizole, Famprofazone, Feprazone, Kebuzone, Metamizole, Mofebutazone, Morazone, Nifenazone, Oxyphenbutazone, Phenazone, Phenylbutazone, Propyphenazone, Sulfinpyrazone, Suxibuzone, Aspirin, Aloxiprin, Benorylate, Carbasalate, calcium Diflunisal, Dipyrocetyl, Ethenzamide, Guacetisal, Magnesium salicylate, Methyl salicylate, Salsalate, Salicin, Salicylamide, Salicylic acid (salicylate), Sodium salicylate, Aceclofenac, Acemetacin, Alclofenac, Amfenac, Bendazac, Bromfenac, Bumadizone, Bufexamac, Diclofenac, Difenpiramide, Etodolac, Felbinac, Fenclozic acid, Fentiazac, Indomethacin, Indomethacin farnesil, Isoxepac, Ketorolac, Lonazolac, Oxametacin, Prodolic acid, Proglumetacin, Sulindac, Tiopinac, Tolmetin, Zomepirac, Ampiroxicam, Droxicam, Isoxicam, Lornoxicam, Meloxicam, Piroxicam, Tenoxicam, Alminoprofen, Benoxaprofen, Carprofen, Dexibuprofen, Dexketoprofen, Fenbufen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Pirprofen, Suprofen, Tarenflurbil, Tepoxalin, Tiaprofenic acid, Vedaprofen, Naproxcinod, Azapropazone, Clonixin, Etofenamate, Flufenamic acid, Flunixin, Meclofenamic acid, Mefenamic acid, Morniflumate, Niflumic acid, Tolfenamic acid, Flutiazin, Apricoxib, Celecoxib, Cimicoxib, Deracoxib, Etoricoxib, Firocoxib, Lumiracoxib, Mavacoxib, Parecoxib, Robenacoxib, Rofecoxib, Valdecoxib, Aminopropionitrile, Benzydamine, Chondroitin sulfate, Diacerein, Fluproquazone, Glucosamine, Glycosaminoglycan, Hyperforin, Nabumetone, Nimesulide, Oxaceprol, Proquazone, Superoxide dismutase/Orgotein, and Tenidap. Examples of glucocorticoids include but are limited to betamethasone and prednisone. Examples of biological response modifiers include but are not limited to hydroxychloroquine, leflunomide, methotrexate, tofacitinib, abatacept, adalimumab, adalimumab-atto, anakinra, etanercept, etanercept-szzs, rituximab, infliximab-dyyb, golimumab, certolizumab pegol, tocilizumab, and sarilumab. Example of opioidsinclude but are not limited to tramadol, oxycontin, oxycodone, fentanyl, morphine, codeine, dihydrocodeine, and actiq.

In a particular embodiment, the disclosure provides for a method to attenuate macrophage inflammation and/or suppress the secretion of pro-inflammatory cytokines in a subject suffering from pain, comprising administering to the subject an effective amount of an oligosaccharide, or a pharmaceutical composition comprising the oligosaccharide, wherein the oligosaccharide comprises a structure of Formula I, I(a) or II:

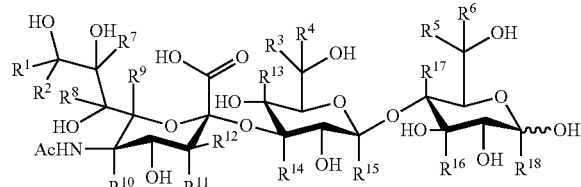

Formula I

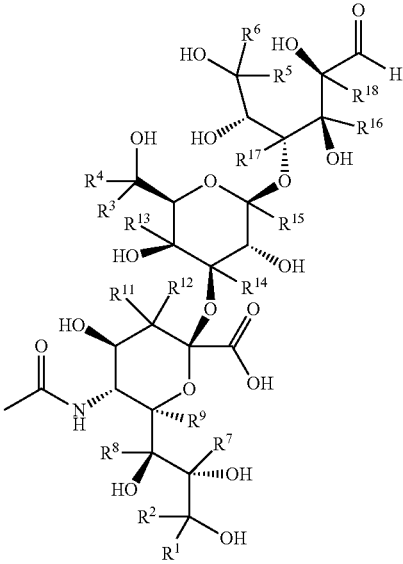

Formula I(a)

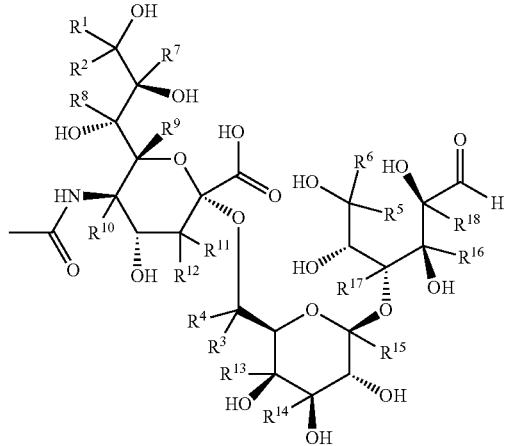

Formula II or a pharmaceutically acceptable salt, solvate, or prodrug thereof, wherein, $R^1$-$R^{18}$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$) cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a ($C_1$-$C_5$)alkyl; and R' is independently selected from H, D, an unsubstituted or substituted ($C_1$-$C_6$) alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, and an unsubstituted or substituted aryl. In another embodiment, the disclosure provides for a method to attenuate macrophage inflammation and/or suppress the secretion of pro-inflammatory cytokines in a subject in need thereof, comprising administering to the subject an effective amount of an oligosaccharide, or a pharmaceutical composition comprising the oligosaccharide, wherein the oligosaccharide comprises a structure of Formula I(b) or I(c):

$C_6$)heteroalkynyl, an unsubstituted or substituted ($C_4$-$C_8$) cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a ($C_1$-$C_5$)alkyl; and R' is independently selected from H, D, an unsubstituted or substituted ($C_1$-$C_6$) alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, and an unsubstituted or substituted aryl. In yet another embodiment, the disclosure provides for a method to attenuate macrophage inflammation and/or suppress the secretion of pro-inflammatory cytokines in a subject in need thereof, comprising administering to the subject an effective amount of an oligosaccharide, or a pharmaceutical composition comprising the oligosaccharide, wherein the oligosaccharide comprises a structure of Formula I(d), I(e) or II(a):

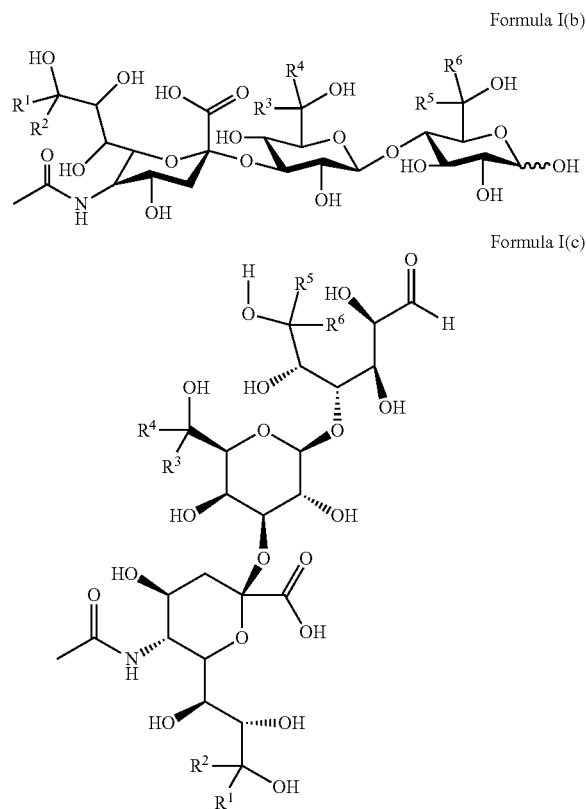

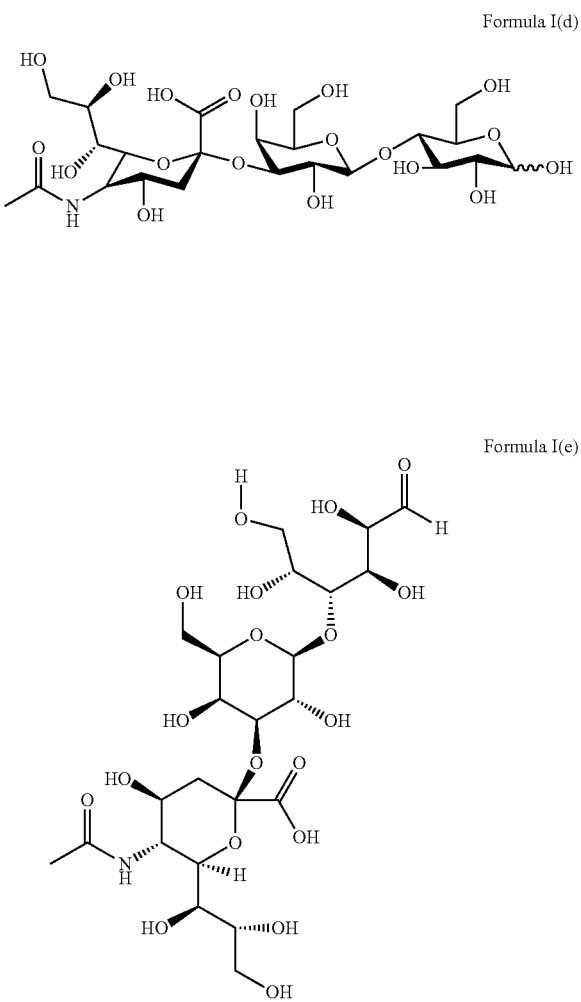

or a pharmaceutically acceptable salt, solvate, or prodrug thereof, wherein, $R^1$-$R^6$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-

Formula II(a)

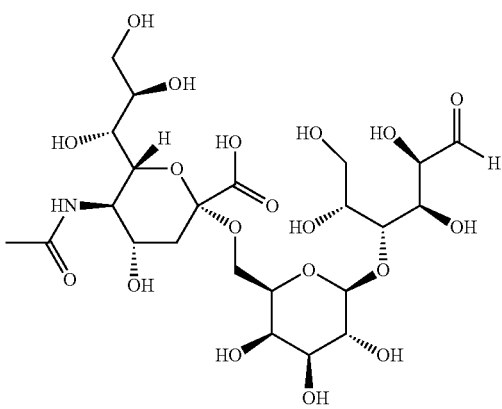

or a pharmaceutically acceptable salt, solvate, or prodrug thereof. In yet a further embodiment, the pro-inflammatory cytokines comprise interleukin (IL)-1β and IL-6. In a certain embodiment, fora method disclosed herein an oligosaccharide of disclosure, or a pharmaceutical composition comprising the oligosaccharide of disclosure, is administered to a human subject that is 5 years of age or older (e.g., 6, 7, 8, 9, 10, 11, 12 years of age or older).

In an alternative embodiment, the composition comprising the oligosaccharide(s) are administered to a subject less than 5 years of age.

In a further embodiment, for a method disclosed herein an oligosaccharide of disclosure, or a pharmaceutical composition comprising the oligosaccharide of disclosure, is administered to a human subject that is 18 years of age or older.

DETAILED DESCRIPTION

Figure 1A:
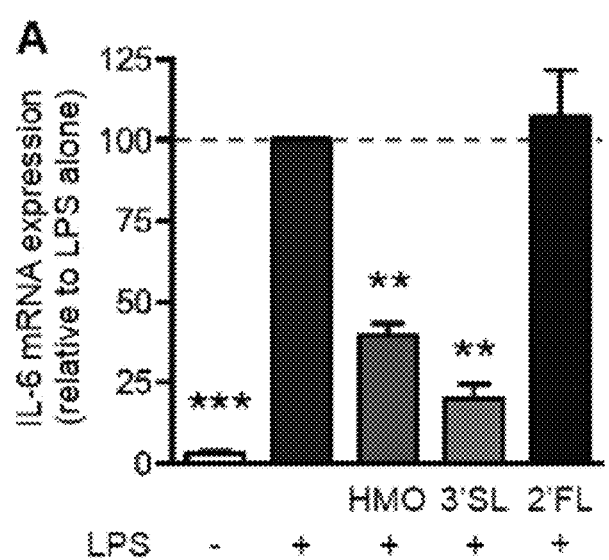
FIG. 1A-C demonstrates that 3'-sialyllactose (3' SL) reduces IL-6 and IL-1β mRNA expression in LPS-activated macrophages. RAW246.7 cells were exposed to LPS either alone or in combination with either pooled human milk oligosaccharides (HMOs), or 3'-sialyllactose (3'SL) or 2'-fucosyllactose (2'FL). After 6 hours, IL-6 (A) and IL-1β (B) mRNA levels were measured by RT-PCR and are plotted as mean±standard deviation (n=8) relative the respective mRNA levels in cells that were exposed to LPS alone (p<0.01; *p<0.001). HMOs are a group of more than 150 different structurally distinct oligosaccharides and their composition follows a basic structural blueprint (C), containing five monosaccharide building blocks: glucose (dark gray circle), galactose (light gray circle), N-acetylglucosamine (dark gray square), fucose (gray triangle) and sialic acid (gray diamond). 3'SL contains lactose with sialic acid at the terminal end; 2'FL contains lactose with fucose at the terminal end.

As used herein and in the appended claims, the singular forms "a," "an," and "the" include plural referents unless the context clearly dictates otherwise. Thus, for example, reference to "an oligosaccharide" includes a plurality of such oligosaccharides and reference to "the therapeutic agent" includes reference to one or more therapeutic agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of." The term "consisting essentially," when used in the context of a list of active and inactive components in a composition or formulation is intended to exclude active components that are not listed. For example, a composition "consisting essentially of" 3-SL is intended to exclude compositions containing other HMOs.

Unless defined otherwise, all technical and scientific terms used herein have the same meaning as commonly understood to one of ordinary skill in the art to which this disclosure belongs.

Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, for terms expressly defined in this disclosure, the definition of the term as expressly provided in this disclosure will control in all respects, even if the term has been given a different meaning in a publication, dictionary, treatise, and the like.

The term "alkenyl", refers to an organic group that is comprised of carbon and hydrogen atoms that contains at least one double covalent bond between two carbons. Typically, an "alkenyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkenyl can form a double bond to a carbon of a parent chain, an alkenyl group of three or more carbons can contain more than one double bond. In certain instances, the alkenyl group will be conjugated, in other cases an alkenyl group will not be conjugated, and yet other cases the alkenyl group may have stretches of conjugation and stretches of non-conjugation. Additionally, if there is more than 2 carbons, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkyl" refers to an organic group that is comprised of carbon and hydrogen atoms that contains single covalent bonds between carbons. Typically, an "alkyl" as used in this disclosure, refers to an organic group that contains 1, 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkynyl can form a triple bond to a carbon of a parent chain, an alkynyl group of four or more carbons can contain more than one triple bond. Where if there is more than 3 carbons, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 4 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompasses from 1 to 4 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O. In a particular embodiment, a "hetero"-hydrocarbon (e.g., alkyl, alkenyl, alkynyl) refers to a hydrocarbon that has from 1 to 3 C, N and/or S atoms as part of the parent chain.

The term "heterocycle," as used herein, refers to ring structures that contain at least 1 noncarbon ring atom. A "heterocycle" for the purposes of this disclosure encompass from 1 to 4 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O.

Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1] heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "non-release controlling excipient" as used herein, refers to an excipient whose primary function do not include modifying the duration or place of release of the active substance from a dosage form as compared with a conventional immediate release dosage form.

The term "optionally substituted" refers to a functional group, typically a hydrocarbon or heterocycle, where one or more hydrogen atoms may be replaced with a substituent. Accordingly, "optionally substituted" refers to a functional group that is substituted, in that one or more hydrogen atoms are replaced with a substituent, or unsubstituted, in that the hydrogen atoms are not replaced with a substituent. For example, an optionally substituted hydrocarbon group refers to an unsubstituted hydrocarbon group or a substituted hydrocarbon group.

The term "pharmaceutically acceptable carrier," "pharmaceutically acceptable excipient," "physiologically acceptable carrier," or "physiologically acceptable excipient" as used herein, refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. Examples of "pharmaceutically acceptable carriers" and "pharmaceutically acceptable excipients" can be found in the following, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004.

The term "release controlling excipient" as used herein, refers to an excipient whose primary function is to modify the duration or place of release of the active substance from a dosage form as compared with a conventional immediate release dosage form. The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

The term "substantially pure" as used herein in reference to a given oligosaccharide means that the oligosaccharide is substantially free from other biological macromolecules. The substantially pure oligosaccharide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The term "substituent" refers to an atom or group of atoms substituted in place of a hydrogen atom. For purposes of this invention, a substituent would include deuterium atoms.

The term "substituted" with respect to hydrocarbons, heterocycles, and the like, refers to structures wherein the parent chain contains one or more substituents.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

The terms "treat", "treating" and "treatment", as used herein, refers to ameliorating symptoms associated with a disease or disorder (e.g., arthritis), including preventing or delaying the onset of the disease or disorder symptoms, and/or lessening the severity or frequency of symptoms of the disease or disorder.

The term "unsubstituted" with respect to hydrocarbons, heterocycles, and the like, refers to structures wherein the parent chain contains nosubstituents.

The terms "active ingredient" and "active substance" refer to an oligosaccharide or compound, which is administered, alone or in combination with one or more pharmaceutically acceptable excipients and/or carriers, to a subject for treating, preventing, or ameliorating one or more symptoms of a disorder.

The terms "drug," or "therapeutic agent," refer to a compound, or a pharmaceutical composition thereof, which is administered to a subject for treating, preventing, or ameliorating one or more symptoms of a disorder.

The term "disorder" as used herein is intended to be generally synonymous, and is used interchangeably with, the terms "disease," "syndrome" and "condition" (as in medical condition), in that all reflect an abnormal condition of the body or of one of its parts that impairs normal functioning and is typically manifested by distinguishing signs and symptoms.

Rheumatoid arthritis (RA) is a lifelong, systemic autoimmune disease that affects women three times more frequently than men, often in their most productive and childbearing years. Pregnancy in women with RA poses a therapeutic challenge. Some anti-rheumatic drugs can cross the placenta and harm the fetus and/or are transferred into breast milk and harm the breastfed baby. Teratogenic compounds like methotrexate and leflunamide are to be avoided and high dose steroids may be associated with a premature rupture of the membranes. The high risk of drug transfer into breast milk often leads to the recommendation for women to cease breastfeeding. Pregnant patients can experience an improvement in symptoms of RA or even go into complete remission. There are several mechanisms that have been attributed to this phenomenon including paternal HLA type, hormones and switches in T cell subtypes.

The disclosure demonstrates that 3'- and/or 6'-sialyllactose have anti-inflammatory effects in macrophages and alleviates paw swelling and cartilage damage in mice. 3'- and/or 6'-sialyllactose (3' SL and 6' SL, respectively) were found to be an anti-inflammatory agent that reduced pro-inflammatory cytokine expression in activated macrophages in vitro and when given orally, alleviate paw swelling and cartilage damage in the collagen antibody-induced arthritis (CAIA) mouse model in vivo.

Oral administration of the oligosaccharides of the disclosure provide for systemic circulation of the oligosaccharides both in infants and adults. Unlike other drug products approved by the FDA, the oligosaccharides described herein can not only be administered to treat a disease or disorder in an adult subject, but can also be administered to pregnant females, infants, and subjects who have impaired organ function (e.g., liver disfunction, kidney failure). The efficacy of oligosaccharides of disclosure as therapy for treating RA is demonstrated herein. Due to the oligosaccharides of the disclosure having little to no adverse effects in humans, this form of therapy could be used as a preventive, as a first line therapy option, or as an adjunct to existing therapies that would be well tolerated by patients of either sex.

In a particular embodiment, the disclosure provides for an oligosaccharide having the structure of Formula I, I(a) or II:

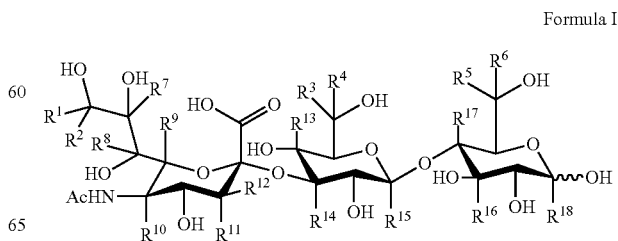

Formula I

-continued

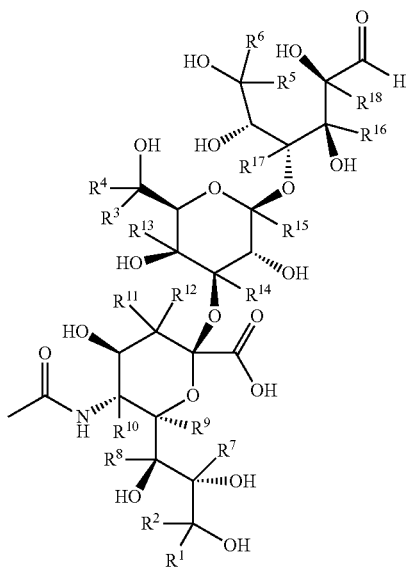

Formula I(a)

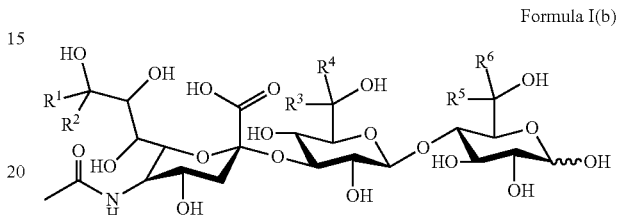

Formula I(b)

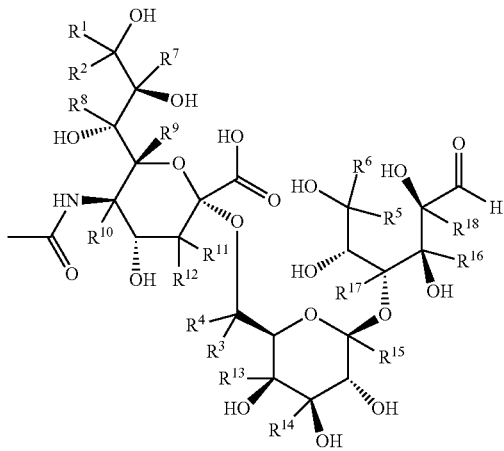

Formula II

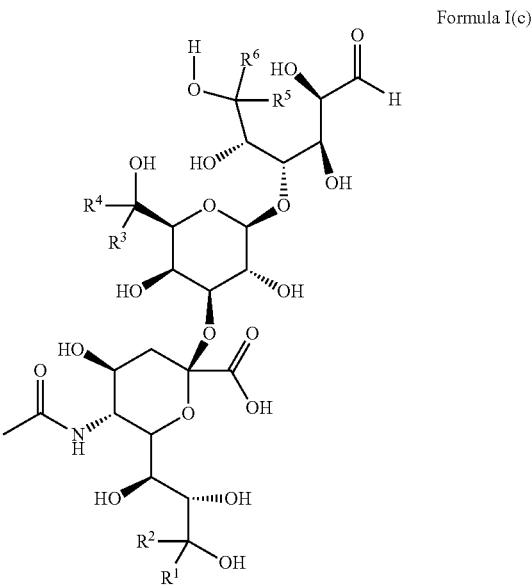

Formula I(c)

or a pharmaceutically acceptable salt, solvate, or prodrug thereof, wherein, $R^1$-$R^6$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a ($C_1$-$C_5$)alkyl;

R' is independently selected from H, D, an unsubstituted or substituted ($C_1$-$C_6$) alkyl, an unsubstituted or substituted ($C_1$-$C_6$)heteroalkyl, an unsubstituted or substituted (2-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$) heteroalkynyl, an unsubstituted or substituted ($C_4$-$C_8$) cycloalkyl an unsubstituted or substituted heterocycle, and an unsubstituted or substituted aryl.

In a certain embodiment, the disclosure provides for an oligosaccharide having the structure of Formula I(b) or I(c):

or a pharmaceutically acceptable salt, solvate, or prodrug thereof, wherein, $R^1$-$R^6$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$; R is absent or a (C$_1$-C$_5$)alkyl; R' is independently selected from H, D, an unsubstituted or substituted (C$_1$-C$_6$) alkyl, an unsubstituted or substituted (C$_1$-C$_6$)heteroalkyl, an unsubstituted or substituted (C$_2$-C$_6$)alkenyl, an unsubstituted or substituted (C$_2$-C$_6$)heteroalkenyl, an unsubstituted or substituted (C$_3$-C$_6$)alkynyl, an unsubstituted or substituted (C$_3$-C$_6$)heteroalkynyl, an unsubstituted or substituted (C$_4$-C$_8$)cycloalkyl, an unsubstituted or substituted heterocycle, and an unsubstituted or substituted aryl.

In a particular embodiment, the disclosure provides for a method disclosed herein which comprises administering a 3'-sialyllactose (3'SL)-based oligosaccharide disclosed herein or a pharmaceutical composition comprising a 3'-sialyllactose (3'SL)-based oligosaccharide disclosed herein.

In another embodiment, the disclosure also provides for a method disclosed herein which comprises administering one or more oligosaccharides having the structure of Formula I, I(a) and/or II:

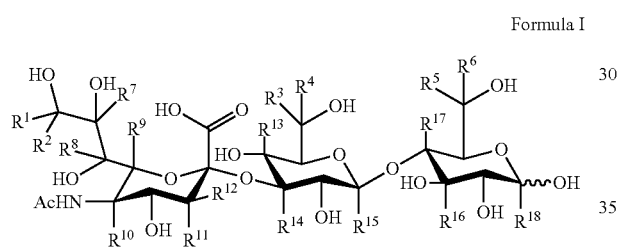

Formula I

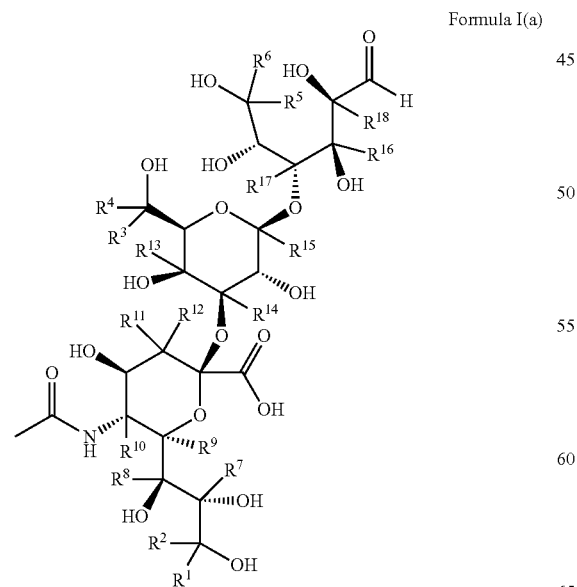

Formula I(a)

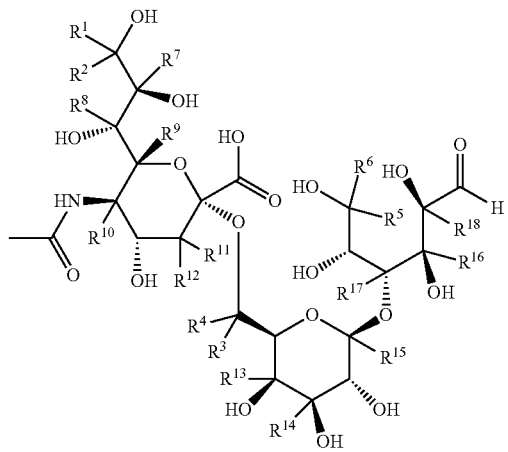

Formula II or a pharmaceutically acceptable salt, solvate, or prodrug thereof, wherein, R$^1$-R$^{18}$ are independently selected from H, D, a halo, an unsubstituted or substituted (C$_1$-C$_6$)alkyl, an unsubstituted or substituted (C$_1$-C$_6$)heteroalkyl, an unsubstituted or substituted (C$_2$-C$_6$)alkenyl, an unsubstituted or substituted (C$_2$-C$_6$)heteroalkenyl, an unsubstituted or substituted (C$_3$-C$_6$)alkynyl, an unsubstituted or substituted (C$_3$-C$_6$)heteroalkynyl, an unsubstituted or substituted (C$_4$-C$_8$)cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$;

R is absent or a (C$_1$-C$_5$)alkyl;

R' is independently selected from H, D, an unsubstituted or substituted (C$_1$-C$_6$) alkyl, an unsubstituted or substituted (C$_1$-C$_6$)heteroalkyl, an unsubstituted or substituted (C$_2$-C$_6$)alkenyl, an unsubstituted or substituted (C$_2$-C$_6$)heteroalkenyl, an unsubstituted or substituted (C$_3$-C$_6$)alkynyl, an unsubstituted or substituted (C$_3$-C$_6$) heteroalkynyl, an unsubstituted or substituted (C$_4$-C$_8$) cycloalkyl, an unsubstituted or substituted heterocycle, and an unsubstituted or substituted aryl. In an alternate embodiment, the disclosure further provides for a method disclosed herein which comprises administering a pharmaceutical composition which comprises one or more oligosaccharides having the structures of Formula I, I(a) and/or II or a pharmaceutically acceptable salt, solvate, or prodrug thereof. In another embodiment, the disclosure also provides for a method disclosed herein which comprises administering one or more oligosaccharides having the structure of Formula I(b) and/or I(c):

Formula I(b)

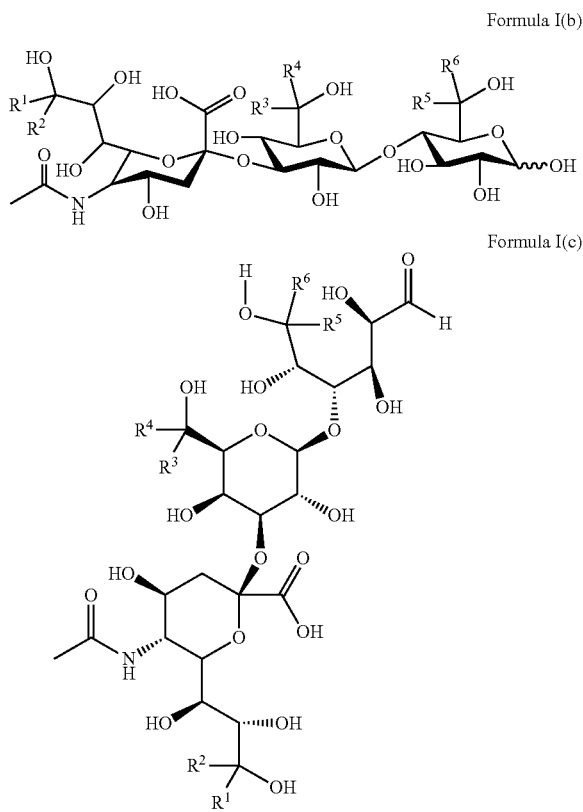

Formula I(c)

or a pharmaceutically acceptable salt, solvate, or prodrug thereof, wherein, $R^1$-$R^6$ are independently selected from H, D, a halo, an unsubstituted or substituted ($C_1$-$C_6$)alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$)heteroalkynyl, an unsubstituted or substituted ($C_4$-$C_8$)cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, (=O)R', —RNO$_2$, —RSR', —RCN, —RNC, —RNNR', —RC(=O)OR', —ROC(=O)R', —RC(=O)H, —RC(=O)OH, —RC(=O)N(R')$_2$, —RN$_3$, —ROCN, —RNCO, —RONO$_2$, —RNO, —ROP(=O)(OH)$_2$, and —RB(OH)$_2$;

R is absent or a ($C_1$-$C_5$)alkyl;

R' is independently selected from H, D, an unsubstituted or substituted ($C_1$-$C_6$) alkyl, an unsubstituted or substituted ($C_1$-$C_6$)heteroalkyl, an unsubstituted or substituted ($C_2$-$C_6$)alkenyl, an unsubstituted or substituted ($C_2$-$C_6$)heteroalkenyl, an unsubstituted or substituted ($C_3$-$C_6$)alkynyl, an unsubstituted or substituted ($C_3$-$C_6$) heteroalkynyl, an unsubstituted or substituted ($C_4$-$C_8$) cycloalkyl, an unsubstituted or substituted heterocycle, and an unsubstituted or substituted aryl. In an alternate embodiment, the disclosure further provides for a method disclosed herein which comprises administering a pharmaceutical composition which comprises one or more oligosaccharides having the structure of Formula I(b) and/or I(c) or a pharmaceutically acceptable salt, solvate, or prodrug thereof.

In yet another embodiment, the disclosure provides for a method disclosed herein which comprises administering one or more oligosaccharide having the structures of Formula I(d), I(e) and/or II(a):

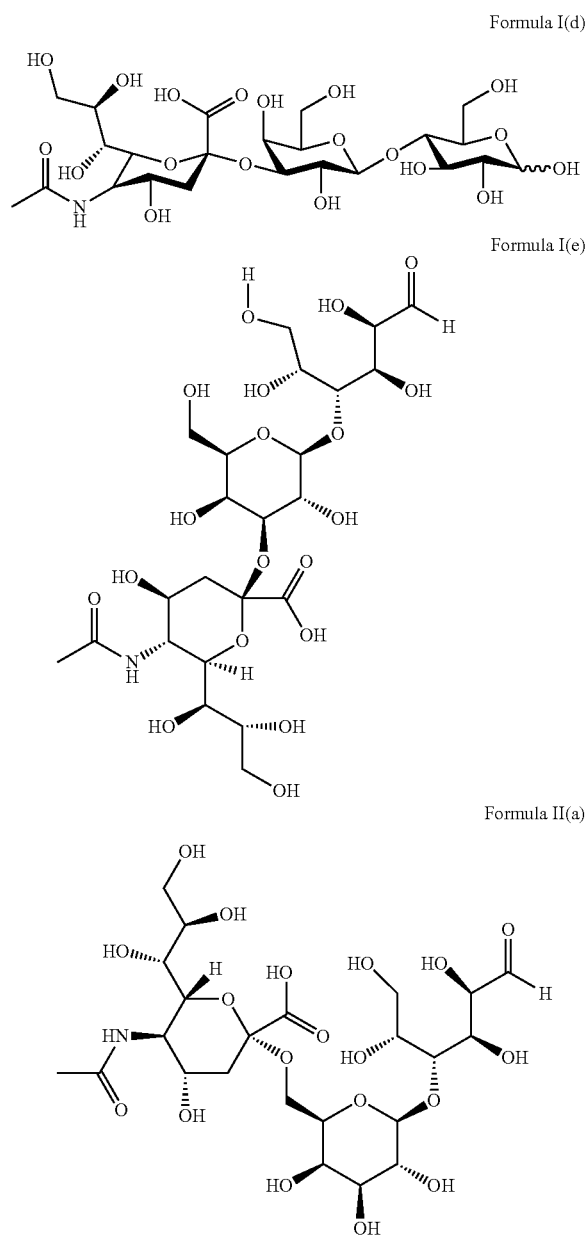

Formula I(d)

Formula I(e)

Formula II(a)

or a pharmaceutically acceptable salt, solvate, or prodrug thereof.

In an alternate embodiment, the disclosure also provides for a method disclosed herein which comprises administering a pharmaceutical composition which comprises one or more oligosaccharides of Formula I(d), I(e) and/or II(a) or a pharmaceutically acceptable salt, solvate, or prodrug thereof.

In a further embodiment, said oligosaccharide is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

The oligosaccharides disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of an oligosaccharide in its (R) form is equivalent, for oligosaccharides that undergo epimerization in vivo, to administration of the oligosaccharide in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the oligosaccharide disclosed herein contains an acidic or basic moiety, it may also be disclosed as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The oligosaccharide as disclosed herein may also be designed as a prodrug, which is a functional derivative of the oligosaccharide as disclosed herein and is readily convertible into the parent oligosaccharide in vivo. Prodrugs are often useful because, in some situations, they may be easier to administer than the parent oligosaccharide. They may, for instance, be bioavailable by oral administration whereas the parent oligosaccharide is not.

The prodrug may also have enhanced solubility in pharmaceutical compositions over the parent oligosaccharide. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnej ad in "Transport Processes in Pharmaceutical Systems," Amidon et al., Ed., Marcell Dekker, 185-218, 2000; Balant et al., *Eur. J. Drug. Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The oligosaccharide may be produced by biotechnological means using enzyme-based fermentation technology (recombinant or natural enzymes) or microbialfermentation technology. In the latter case, microbes may either express their natural enzymes and substrates or may be engineered to produce respective substrates and enzymes. Single microbial cultures and/or mixed cultures may be used. Alternatively, the oligosaccharides may be produced by chemical synthesis from lactose and other substrates.

Biotechnological approaches have made it possible for the large scale, cost-efficient production of target oligosaccharides.

Precisely, the oligosaccharides disclosed herein can be produced in high yields in aqueous media by fermentation of genetically modified bacteria, yeasts or other microorganisms. See, for example, WO200104341; WO2007101862, WO2010070104; WO2010142305; WO2012112777; Priem et al., *Glycobiology* 12:235 (2002); Drouillard et al., *Angew. Chem. Int. Ed.* 45:1778 (2006); Han et al., *Biotechnol. Adv.* 30:1268 (2012); Lee et al., *Microb. Cell Fact.* 11:48 (2012); Baumgartner et al., *Microb. Cell Fact.* 12:40 (2013); and WO 2014135167A1.

Alternatively, the oligosaccharides of the disclosure can be synthesized based upon methods described in WO2011100980A1; WO2012007588A1; WO2012127410A1; WO2012155916A1; WO2013044928A1; and U.S. Pat. No. 9,102,966B2. 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410. With a regard to biotechnological methods, WO 2001/04341 and WO 2007/101862 describe how to make oligosaccharides optionally substituted by fucose or sialic acid using genetically modified E. coli.

In a certain embodiment, the disclosure provides for a nutritional composition that comprises one or more oligosaccharides (e.g., 3'SL and/or 6'SL or derivatives thereof) disclosed herein along with one or more foodgrade agents. In certain embodiments, the nutritional composition comprises or consists of 3' SL, 6'SL or a combination of 3' SL and 6'SL. In other embodiments, the nutritional composition comprise or consists of 3'SL, 6'SL or a combination thereof at 145 mg/L or greater of 3'SL, 6'SL or a combination of 3'SL and 6'SL.

In another embodiment, the nutritional composition comprises at least 9% (e.g., 10, 15, 20, 25, 30, 35, 40, 45, 50, 55, 60, 65, 70, 75, 80, 85, 90, 95, or 100%; or any value between any of the foregoing) 3' SL, 6' SL or a combination thereof of the total oligosaccharides in the composition. Examples of foodgrade agents that can be used with the oligosaccharides disclosed herein, include, but are not limited to, milk (e.g., cow's milk, almond milk, soy milk), yogurt, maltodextrin, milk protein concentrate, Sucromalt, glycerine, cocoa powder, soy protein isolate, fructose, vegetable or animal oils (e.g., high oleic safflower oil, soy oil, canola oil), plant sterol esters, HMSs/HMOs, soy lecithin, carrageenan, taurine, L-carnitine, vitamins and/or minerals (e.g., sodium ascorbate, potassium citrate, sodium phosphate, calcium citrate, choline chloride, potassium chloride, sodium citrate, magnesium oxide, alpha-tocopheryl acetate, zinc sulfate, ferrous sulfate, niacinamide, calcium pantothenate, vitamin A palmitate, citric acid, manganese sulfate, pyridoxine hydrochloride, vitamin D3, copper sulfate, thiamine mononitrate, riboflavin, beta carotene, folic acid, biotin, potassium iodide, chromium chloride, sodium selenate, sodium molybdate, phytonadione, vitamin B12, magnesium chloride, calciumphosphate).

Disclosed herein are pharmaceutical compositions comprising one or more oligosaccharides of the disclosure (e.g., 3' SL and/or 6' SL or derivatives thereof), or a pharmaceutically acceptable salt, solvate, or prodrug thereof, as an active ingredient, combined with a pharmaceutically acceptable vehicle, carrier, diluent, or excipient, or a mixture thereof; in combination with one or more pharmaceutically acceptable excipients or carriers.

Disclosed herein are pharmaceutical compositions in modified release dosage forms, which comprise one or more oligosaccharides (e.g., 3' SL and/or 6' SL or derivatives thereof) of the disclosure, or a pharmaceutically acceptable salt, solvate, or prodrug thereof; and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise one or more oligosaccharides (e.g., 3' SL and/or 6' SL or derivatives thereof) as disclosed herein, or a pharmaceutically acceptable salt, solvate, or prodrug thereof; and one or more release controlling excipients or carriers for use in an enteric coated dosage form. The pharmaceutical compositions may also comprise non-release controlling excipients or carriers.

Further disclosed herein are pharmaceutical compositions in effervescent dosage forms, which comprise one or more oligosaccharides (e.g., 3' SL and/or 6' SL or derivatives thereof) as disclosed herein in substantially pure form (e.g., lacking other oligosaccharides found in milk), or a pharmaceutically acceptable salt, solvate, or prodrug thereof; and one or more release controlling excipients or carriers for use in an effervescent dosage form. The pharmaceutical compositions may also comprise non-release controlling excipients or carriers.

Additionally, disclosed are pharmaceutical compositions in a dosage form that has an instant releasing component and at least one delayed releasing component, and is capable of giving a discontinuous release of one or more oligosaccharides (e.g., 3'SL and/or 6' SL or derivatives thereof) disclosed herein in the form of at least two consecutive pulses separated in time (e.g., separated in time from 0.1 up to 24 hours or a few days). The pharmaceutical compositions comprise an oligosaccharide as disclosed herein, or a pharmaceutically acceptable salt, solvate, or prodrug thereof; and one or more release controlling and non-release controlling excipients or carriers, such as those excipients or carriers suitable for a disruptable semi-permeable membrane and as swellable substances.

Disclosed herein also are pharmaceutical compositions in a dosage form for oral administration to a subject, which comprise one or more oligosaccharides (e.g., 3' SL and/or 6' SL or derivative thereof) as disclosed herein, or a pharmaceutically acceptable salt, solvate, or prodrug thereof; and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Provided herein are pharmaceutical compositions that comprise about 0.1 to about 1000 mg or up to 2000 mg or up to 3000 mg (or any value between 0.1-3000 mg), about 1 to about 500 mg, about 2 to about 100 mg, about 1 mg, about 2 mg, about 3 mg, about 5 mg, about 10 mg, about 15 mg, about 20 mg, about 30 mg, about 40 mg, about 50 mg, about 100 mg, about 500 mg of one or more oligosaccharides as disclosed herein, in the form of immediate release tablets for oral administration. The pharmaceutical compositions further comprise inactive ingredients such as flavoring agents, copovidone, ethylcellulose, magnesium stearate, mannitol, and silicon dioxide.

Provided herein are pharmaceutical compositions that comprise about 0.1 to about 1000 mg or up to 2000 mg or up to 3000 mg (or any value there between), about 1 to about 500 mg, about 2 to about 100 mg, about 1 mg, about 2 mg, about 3 mg, about 5 mg, about 10 mg, about 15 mg, about 20 mg, about 30 mg, about 40 mg, about 50 mg, about 100 mg, about 500 mg of one or more oligosaccharides as disclosed herein, in the form of extended release tablets for oral administration. The pharmaceutical compositions further comprise inactive ingredients such as ethylcellulose, dibutyl sebacate, polyvinyl pyrroliodone, sodium stearyl fumarate, colloidal silicon dioxide, and polyvinylalcohol.

The pharmaceutical compositions disclosed herein may be disclosed in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the oligosaccharide sufficient to produce the desired therapeutic effect, in association with the required pharmaceutical carriers or excipients. Examples of unit-dosage forms include ampoules, syringes, and individually packaged to capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The oligosaccharides as disclosed herein may be administered alone, or in combination with one or more other oligosaccharides disclosed herein, and/or one or more other active ingredients. The pharmaceutical compositions that comprise an oligosaccharide disclosed herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms.

These dosage forms can be prepared according to conventional methods and techniques known to those skilled in the art (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the oligosaccharides may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the oligosaccharides may be given continuously or temporarily suspended for a certain length of time (i.e., a "drug holiday").

Once improvement of the patient's condition has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The pharmaceutical compositions disclosed herein may be formulated in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastimes, cachets, pellets, medicated chewing gum, granules, bulk powders, effervescent or non-effervescent powders or granules, solutions, emulsions, suspensions, solutions, wafers, sprinkles, elixirs, and syrups. In addition to the oligosaccharides, the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethyl cellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethyl cellulose (HEC), hydroxypropyl cellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such asmannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of adisintegrant.

Suitable lubricants include, but are not limited to, calcium stearate; magnesium stearate; mineral oil; light mineral oil;

glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB-O-SIL® (Cabot Co. of Boston, Mass.), and asbestos-free talc.

Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carboxymethylcellulose, hydroxypropyl methylcellulose, and polyvinylpyrrolidone. Preservatives include glycerin, methyl and propylparaben, benzoic add, sodium benzoate and alcohol.

Wetting agents include propylene glycol monostearate, sorbitan monooleate, diethylene glycol monolaurate, and polyoxyethylenelauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation. The pharmaceutical compositions disclosed herein may be formulated as compressed tablets, tablet triturates, chewable lozenges, rapidly dissolving tablets, multiple compressed tablets, or enteric-coating tablets, sugar-coated, or film-coated tablets.

Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates.

Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions disclosed herein may be formulated as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions disclosed herein may be formulated in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative.

Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) disclosed herein, and a dialkylated mono- or polyalkylene glycol.

The pharmaceutical compositions disclosed herein for oral administration may be also formulated in the forms of liposomes, micelles, microspheres, or nanosystems. Micellar dosage forms can be prepared as described in U.S. Pat. No. 6,350,458.

The pharmaceutical compositions disclosed herein may be formulated as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein can be formulated as an oral nutritional composition. An oral nutritional composition can contain sources of protein, lipids and/or digestible carbohydrates and can be in solid, powdered or liquid forms. The composition can be designed to be the sole source of nutrition or a nutritional supplement. Suitable protein sources include intact, hydrolyzed, and partially hydrolyzed protein, which can be derived from any suitable source such as milk (e.g., casin, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, and acid.

The pharmaceutical compositions disclosed herein may be formulated as immediate or modified release dosage forms, including delayed-, sustained-, pulsed-, controlled, targeted-, and programmed-release forms.

The pharmaceutical compositions disclosed herein may be co-formulated with other active ingredients which do not impair the desired therapeutic action, or with substances that supplement the desired action.

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungi static concentrations. All parenteral formulations must be sterile, as known and practiced in the art.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

The pharmaceutical compositions disclosed herein may be administered topically to the skin, orifices, or mucosa. The topical administration, as used herein, include (intra) dermal, conjunctival, intracorneal, intraocular, ophthalmic, auricular, transdermal, nasal, vaginal, ureteral, respiratory, and rectal administration.

The pharmaceutical compositions disclosed herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions disclosed herein may also comprise liposomes, micelles, microspheres, nanosystems, and mixtures thereof.

Pharmaceutically acceptable carriers and excipients suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions disclosed herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

The pharmaceutical compositions disclosed herein may be administered ophthalmically in the forms of solutions, suspensions, ointments, emulsions, gel-forming solutions, powders for solutions, gels, ocular inserts, and implants.

The pharmaceutical compositions disclosed herein may be administered intranasally or by inhalation to the respiratory tract. The pharmaceutical compositions may be formulated in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be formulated as a dry powder for insufflation, alone or in combination with an inert carrier such as lactose or phospholipids; and nasal drops. For intranasal use, the powder may comprise a bioadhesive agent, including chitosan or cyclodextrin.

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route.

Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

The pharmaceutical compositions disclosed herein in a modified release dosage form may be prepared by methods known to those skilled in the art, including direct compression, dry or wet granulation followed by compression, melt-granulation followed by compression.

The pharmaceutical compositions disclosed herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Provided herein are immunomodulatory oligosaccharides that provide for the modulation of a subject's immune system. In particular, the oligosaccharides as disclosed herein can be used for immunotherapy. Immunotherapy is the treatment of disease, disorder, or medical condition by either inducing, enhancing, or suppressing an immune response.

Immunomodulatory regimens often have fewer side effects than existing drugs, including less potential for creating resistance when treating microbial disease. In particular, it has been found herein that components of human breast milk, human milk oligosaccharides, can be an effective modulation of inflammatory cytokines, therefore these compounds and derivatives thereof have the potential to treat pain conditions.

It has been found herein, that the oligosaccharides of the disclosure exerted an immunomodulatory effect in an in vivo rheumatoid arthritis model, by significantly lowering the scores for inflammation, erosion and cartilage damage in animals receiving an oligosaccharide of the disclosure (3' SL).

In an alternate embodiment, the disclosure provides methods for treating, preventing, or ameliorating one or more symptoms of an inflammatory disorder or pain comprising administering to a subject having or being suspected of having such a disorder, a therapeutically effective amount of an oligosaccharide as disclosed herein, or a pharmaceutically acceptable salt, solvate, or prodrug thereof.

Generally, the amount of an oligosaccharide disclosed herein required to be administered to the person can vary depending upon factors such as the risk and condition severity, the age of the person, the form of the composition, and other medications being administered to the person. It would be expected that an oligosaccharide described herein should be well tolerated irrespective of the age and condition of the subject. The dosage of oligosaccharide to be administered can readily be set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, the body weight and/or condition of the patient being treated, the severity of the condition, being treated, other ailments and/or diseases of the person, the incidence and/or severity of side effects and the manner of administration. Appropriate dose ranges can be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

Depending on the disorder to be treated and the injection in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.01 to about 2 grams, from about 0.05 to about 1 gram, or from about 10 to about 500 milligrams active ingredient(s) per dosage unit.

In certain embodiments, an appropriate dosage level is about 0.01 to about 5 g/kg patient body weight per day (mg/kg per day), about 0.01 to about 1 g/kg per day, about 0.01 to about 0.5 g/kg per day, or about 0.1 to about 500 mg/kg per day, which may be administered in single or multiple doses. A suitable dosage level may be about 0.1 to about 500 mg/kg per day, about 0.1 to about 250 mg/kg per day, or about 0.1 to about 100 mg/kg per day. Within this range the dosage may be about 0.01 to about 0.1, about 0.1 to about 1.0, about 1.0 to about 10, or about 10 to about 100 mg/kg per day.

The oligosaccharides disclosed herein may also be combined or used in combination with other agents useful in the treatment, prevention, or amelioration of one or more symptoms of an autoimmune disorder and/or inflammatory disorder. Or, by way of example only, the therapeutic effectiveness of one of the oligosaccharides described herein may be enhanced by administration of an adjuvant (i.e., by itself the adjuvant may only have minimal therapeutic benefit, but in combination with another therapeutic agent, the overall therapeutic benefit to the patient is enhanced). Such other agents, adjuvants, or drugs may be administered, by a route and in an amount commonly used therefore, simultaneously or sequentially with an oligosaccharide as disclosed herein. When an oligosaccharide as disclosed herein is used contemporaneously with one or more other drugs, a pharmaceutical composition containing such other drugs in addition to an oligosaccharide disclosed herein may be utilized, but is not required. Accordingly, the pharmaceutical compositions disclosed herein include those that also contain one or more other active ingredients or therapeutic agents, in addition to an oligosaccharide disclosed herein.

In certain embodiments, an oligosaccharide disclosed herein can be combined with one or more anti-inflammatories known in the art, including, but not limited to, non-steroidal anti-inflammatory drugs (e.g., Aminophenazone, Ampyrone, Azapropazone, Clofezone, Difenamizole, Famprofazone, Feprazone, Kebuzone, Metamizole, Mofebutazone, Morazone, Nifenazone, Oxyphenbutazone, Phenazone, Phenylbutazone, Propyphenazone, Sulfinpyrazone, Suxibuzone, Aspirin, Aloxiprin, Benorylate, Carbasalate, calcium Diflunisal, Dipyrocetyl, Ethenzamide, Guacetisal, Magnesium salicylate, Methyl salicylate, Salsalate, Salicin, Salicylamide, Salicylic acid (salicylate), Sodium salicylate, Aceclofenac, Acemetacin, Alclofenac, Amfenac, Bendazac, Bromfenac, Bumadizone, Bufexamac, Diclofenac, Difenpiramide, Etodolac, Felbinac, Fenclozic acid, Fentiazac, Indomethacin, Indomethacin farnesil, Isoxepac, Ketorolac, Lonazolac, Oxametacin, Prodolic acid, Proglumetacin, Sulindac, Tiopinac, Tolmetin, Zomepirac, Ampiroxicam, Droxicam, Isoxicam, Lornoxicam, Meloxicam, Piroxicam, Tenoxicam, Alminoprofen, Benoxaprofen, Carprofen, Dexibuprofen, Dexketoprofen, Fenbufen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Pirprofen, Suprofen, Tarenflurbil, Tepoxalin, Tiaprofenic acid, Vedaprofen, Naproxcinod, Azapropazone, Clonixin, Etofenamate, Flufenamic acid, Flunixin, Meclofenamic acid, Mefenamic acid, Morniflumate, Niflumic acid, Tolfenamic acid, Flutiazin, Apricoxib, Celecoxib, Cimicoxib, Deracoxib, Etoricoxib, Firocoxib, Lumiracoxib, Mavacoxib, Parecoxib, Robenacoxib, Rofecoxib, Valdecoxib, Aminopropionitrile, Benzydamine, Chondroitin sulfate, Diacerein, Fluproquazone, Glucosamine, Glycosaminoglycan, Hyperforin, Nabumetone, Nimesulide, Oxaceprol, Proquazone, Superoxide dismutase/Orgotein, and Tenidap); glucocorticoids (e.g., betamethasone, prednisone); biologic response modifiers (e.g., hydroxychloroquine, leflunomide, methotrexate, tofacitinib, abatacept, adalimumab, adalimumab-atto, anakinra, etanercept, etanercept-szzs, rituximab, infliximab-dyyb, golimumab, certolizumab pegol, tocilizumab, and sarilumab); and opioids (e.g., tramadol, oxycontin, oxycodone, fentanyl, morphine, codeine, dihydrocodeine, actiq).

In another embodiment of the invention, a sialyllactose can be administered to a patient that is contraindicated for NSAID treatment either in place of an NSAID described herein or to reduce the dose of NSAIDs used to treat such patient's signs and symptoms of inflammatory pain. Examples of patients who are contraindicated for NSAID treatment are patients with hypertension, cardiovascular disease, ulcers, platelet disorders (von Willebrand disease, abnormal platelet function from uremia and thrombocytopenia), patients preparing for surgery, patients on anti-clotting medications (warfarin, heparin), cyclosporin, patients who have fluid retention, kidney disease, a history of urticaria, or patients who are pregnant or breastfeeding.

Improvement in pain or reduction of pain through therapeutic intervention in patients are often measured by patient reported outcome measures. In patients with inflammatory pain, including pain associate with osteoarthritis can be measured by one or more of the following patient reported outcome measures: Western Ontario McMaster Osteoarthritis Index (WOMAC), Medical Outcome Studies Short Form 36 (SF-36), Knee Disability and Osteoarthritis Outcome Score (KOOS), Oxford Knee Score (OKS), Disabilities of the Arm, Shoulder and Hand (DASH), EUROQoL (EQ5-D), Medical Outcomes Study Short Form 12-Item (SF-12), Hip Disability and Osteoarthritis Outcome Score (HOOS), Pain Catastrophizing PROM (PCS) or Oxford Hip Score (OHS).

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more oligosaccharides described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise an oligosaccharide with an identifying description or label or instructions relating to its use in the methods described herein.

In certain embodiments, a container consists of 3'SL, 6' SL or a combination of 3' SL and 6' SL. In other embodiments, the container comprises or consists of 3' SL, 6' SL or a combination thereof at 145 mg/L or greater. In another embodiment, the container comprises a composition that is at least 9% (e.g., 10, 15, 20, 25, 30, 35, 40, 45, 50, 55, 60, 65, 70, 75, 80, 85, 90, 95, or 100%; or any value between any of the foregoing) 3' SL, 6' SL or a combination thereof of the total oligosaccharides in the composition.

A kit will typically comprise one or more additional containers, each with one or more of various materials (such as reagents, optionally in concentrated form, and/or devices)

desirable from a commercial and user standpoint for use of an oligosaccharide described herein. Non-limiting examples of such materials include, but are not limited to, buffers, diluents, filters, needles, syringes; carrier, package, container, vial and/or tube labels listing contents and/or instructions for use, and package insert with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Figure 1B:
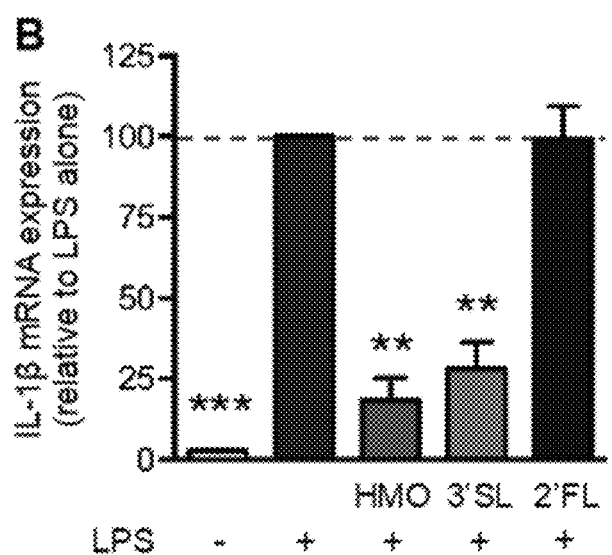

Oligosaccharides Reduce Pro-Inflammatory Cytokine mRNA Expression in Stimulated Macrophages. HMOs were first isolated and purified from pooled human donor milk (pHMO) by using polymixin B affinity chromatography to remove any lipopolysaccharide (LPS) contamination. RAW 264.7 cells, a murine macrophage cell line, were then incubated with LPS (10 ng/mL) and pHMO (500 µg/mL) for 6 hours. RT-PCR was used to measure cytokine mRNA expression. Compared to cells that received LPS alone, cells that were exposed to both LPS and pHMO had significantly reduced mRNA levels for both IL-6 (see FIG. 1A) and IL-1β (see FIG. 1B), two pro-inflammatory cytokines that are of major etiological importance in chronic inflammatory disorders like rheumatic arthritis (RA).

Figure 1C:
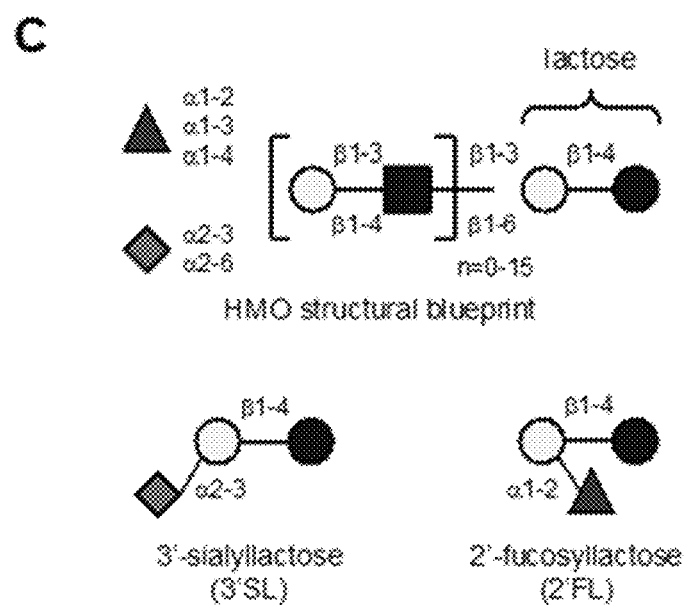

Identification of an Oligosaccharide That Significantly Reduces Pro-Inflammatory Cytokine mRNA Expression in Stimulated Macrophages. A multi-dimensional chromatography approach was used that separates pHMO first by charge and then by size. A specific oligosaccharide, 3' sialyllactose (3'SL), was identified as being the most effective in reducing IL-6 and IL-1β mRNA expression. To exclude that the observed effect was due to impurities or contaminations from the isolation process, the results were confirmed with synthetized and commercially available 3'SL. Dose-range finding studies identified $IC_{50}$ values for 3'SL of around 15 µg/mL. Other oligosaccharides like 2'-fucosyllactose (2'FL), where the terminal monosaccharide is fucose instead of sialic acid (see FIG. 1C), had no effect, emphasizing that the anti-inflammatory effect of 3' SL in macrophages is specific to the structure of 3'SL.

3' SL reduced pro-inflammatory cytokine expression not only in the murine cell line (RAW 264.7), but also in primary mouse cells (bone marrow derived macrophages) and notably in the human THP-1 monocytic cell line, indicating that the effects are not merely a mouse cell line artifact. Accordingly, the results with 3'SL translate to primary cells as well as to human macrophages.

Rheumatoid Arthritis In vivo Experimental Design. Macrophages and the pro-inflammatory cytokines IL-6 and IL-1β are known to perform a major role in the development and progression of joint destruction in animal models and patients with RA. 3'SL significantly reduced IL-6 and IL-1β expression in activated macrophages in vitro as outlined above.

Next, it was asked whether or not the in vitro results translate to an in vivo model. 3' SL efficacy in a collagen antibody-induced arthritis (CAIA) model was tested in mice. In the CAIA model, arthritis is induced by systemic administration of a cocktail of monoclonal antibodies that target various regions of collagen type II, which is one of the major constituents of articular cartilage matrix proteins, followed by the administration of endotoxin (LPS) on day 3. The high uptake rate in the CAIA model and the capacity to synchronize the development of arthritis from the time of antibody injection, makes this a relatively straightforward model that is used to address questions of pathogenic mechanisms and to screen candidate therapeutic agents. 8-week old female BALB/c mice were injected with 1.5 mg of Arthrogen-CIA monoclonal antibody cocktail (Chondrex, Inc.).

Three days later, the mice were injected with 25 µg of LPS. Beginning with the time of LPS administration and followed for the next 11 consecutive days, mice were orally gavaged thrice daily with either 3' SL (20 mg in saline) or saline alone as control. With the tester blinded to the study groups, arthritis in each limb was determined once per day. Disease incidence was scored by assigning each affected wrist or ankle a score of 2 cumulatively to each anatomic joint that showed evidence of arthritis, and a score of 1 was assigned to each digit. By adding together, the scores of all four limbs, the maximum score per mouse is 28. In addition, a caliper was placed across the ankle joint at the widest point to measure ankle thickness in both hind limbs daily. 14 days after antibody cocktail administration, mice were euthanized, and hind paws collected and processed for histology. H&E—as well as Toluidine blue-stained sections were scored from 0 to 4 for inflammation, bone erosion and cartilage depletion based on a previously validated scoring system.

Figure 2A:
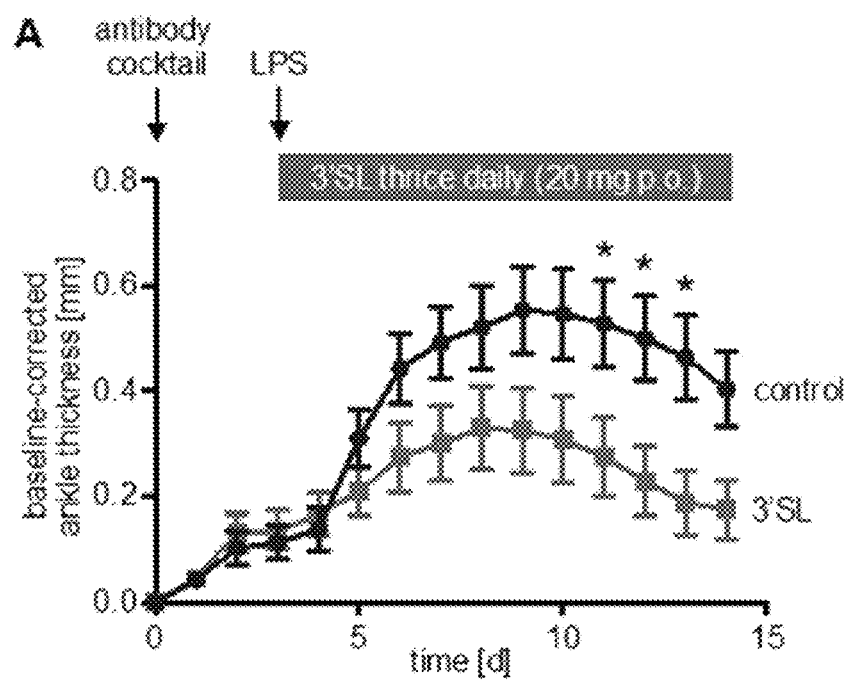
FIG. 2A-C shows that 3'-sialyllactose (3' SL) alleviates paw swelling and cartilage damage in CAIA mouse model. Oral gavage of 3'SL (20 mg thrice daily, beginning at the time of LPS trigger) reduces baseline-corrected ankle swelling (A) and clinical pathology score 28 (B) over the course of the study. 3' SL exposure also significantly reduced hind paw joint inflammation, erosion and cartilage damage measured by histology scores (C). (*p<0.05, p<0.01, *p<0.001).
Figure 2B:
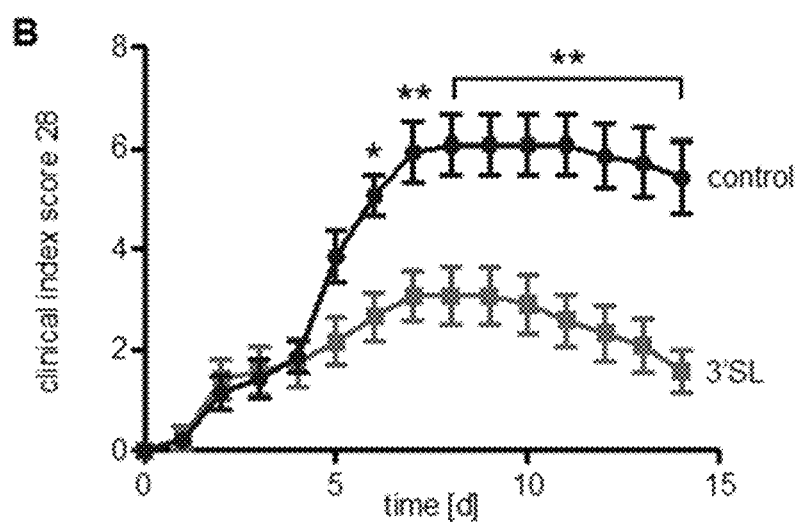
Figure 2C:
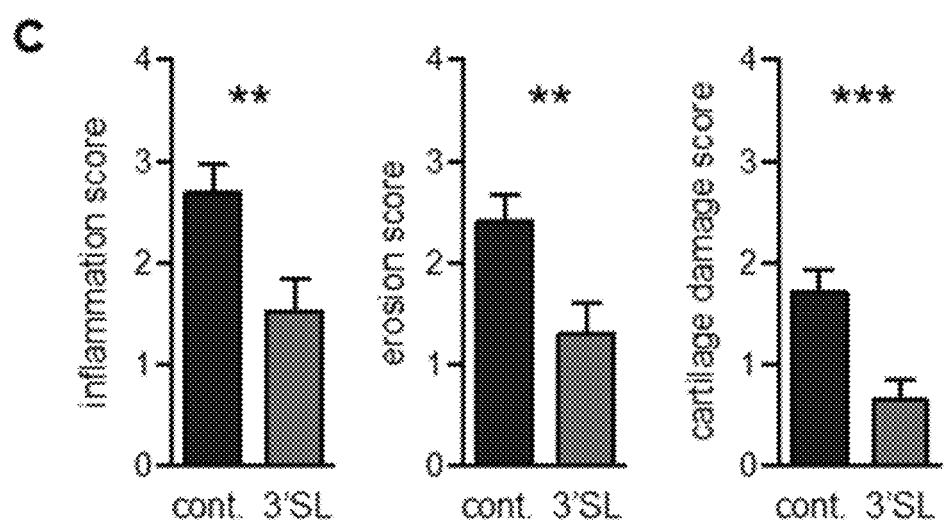

Results of the RA In vivo Model: Baseline-corrected ankle thickness (paw swelling) (FIG. 2A) as well as clinical index score 28 (FIG. 2B) were significantly reduced in the group that received 3'SL. Histological analysis revealed significantly lower scores for inflammation, erosion and cartilage damage in animals receiving 3'SL (FIG. 2C). No adverse effects were observed with 3'SL exposure throughout the 14-day study period.

Models of Inflammatory Pain

The following examples are designed to demonstrate the anti-nociceptive activity of sialyllactose (3'SL, 6' SL or a mixture thereof) (Yin et al. Scientific Reports (2016)6, Article number 27129).

Acetic Acid-Induced Writhing Test

Mice are pretreated with sialyllactose (3'SL, 6' SL or a mixture thereof) by oral or intravenous administration prior to acetic acid treatment according to the methods described in Yin et al.

Sialyllactose treatment causes inhibition of writhing as calculated by:

Inhibition (%)=[(mean number of writhing (control)−mean number of writhing (sialyllactose))/mean number of writhing (control)]×100%.

Formalin Paw Test

Mice are pretreated with sialyllactose (3'SL, 6' SL or a mixture thereof) by oral or intravenous administration prior to formalin injection. The time that the animals spend biting and licking of the injected paw is measured in each group. Less time spent biting and licking the injected paw is a sign of an improvement of nociceptive pain.

Models of Pain Osteoarthritis

The ability of sialyllactose to ameliorate pain in osteoarthritis is evaluated in several animal models of OA associated pain, including spontaneous and induced models of disease described in Kuyinu et al. *J. Orthop. Surg. Res.* (2016)11:19.

It will be understood that various modifications may be made without departing from the spirit and scope of this disclosure. Accordingly, other embodiments are within the scope of the following claims.

What is claimed is:

1. A method of treating inflammatory pain in a patient contraindicated for non-steroidal anti-inflammatory drugs (NSAIDs), comprising administering an effective amount of sialyllactose.

2. The method of claim 1, wherein the sialyllactose compound is a compound selected from a compound of Formula I, I (a) and/or II:

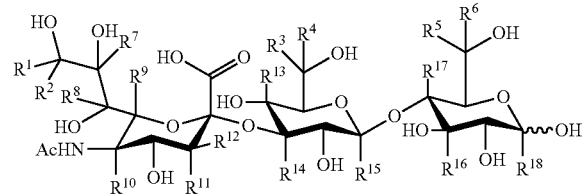
Formula I

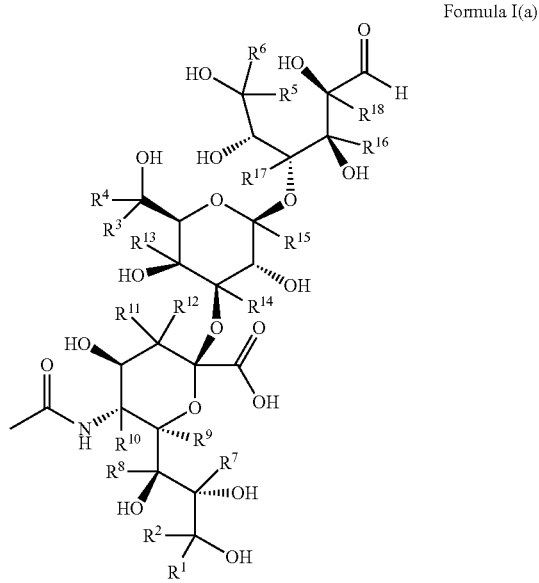
Formula I(a)

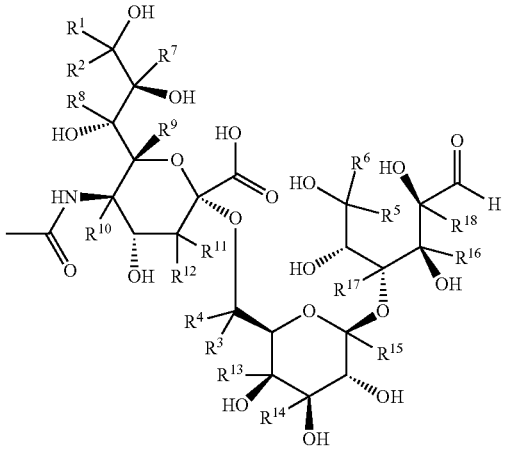
Formula II or a pharmaceutically acceptable salt, solvate, or prodrug thereof, wherein, $R^1$-$R^{18}$ are independently selected from H, D, a halo, an unsubstituted or substituted $C_1$-$C_6$ alkyl, an unsubstituted or substituted $C_1$-$C_6$ heteroalkyl, an unsubstituted or substituted $C_2$-$C_6$ alkenyl, an unsubstituted or substituted $C_2$-$C_6$ heteroalkenyl, an unsubstituted or substituted $C_3$-$C_6$ alkynyl, an unsubstituted or substituted $C_3$-$C_6$ heteroalkynyl, an unsubstituted or substituted $C_4$-$C_8$ cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O) R', —RNO$_2$, —RSR', —RCN, —RNC, —RNNR', —RC(=O) OR', —ROC(=O) R', —RC(=O) H, —RC(=O) OH, —RC(=O) N(R')$_2$, —RN$_3$, —ROCN, —RNCO, —RONO$_2$, —RNO, —ROP (=O) (OH)$_2$, and—RB (OH)$_2$; R is absent or a $C_1$-$C_5$ alkyl; and R' is independently selected from H, D, an unsubstituted or substituted $C_1$-$C_6$ alkyl, an unsubstituted or substituted $C_1$-$C_6$ heteroalkyl, an unsubstituted or substituted $C_2$-$C_6$ alkenyl, an unsubstituted or substituted $C_2$-$C_6$ heteroalkenyl, an unsubstituted or substituted $C_3$-$C_6$ alkynyl, an unsubstituted or substituted $C_3$-$C_6$ heteroalkynyl, an unsubstituted or substituted $C_4$-$C_8$ cycloalkyl, an unsubstituted or substituted heterocycle, and an unsubstituted or substituted aryl.

3. The method of claim 1, wherein the pain is selected from central neuropathic pain, peripheral neuropathic pain, nociceptive pain, mixed pain syndromes, dysfunctional pain, neuropathic headaches, nociceptive headaches and mixed headaches.

4. The method of claim 3, wherein the central neuropathic pain is selected from the group consisting of multiple sclerosis pain, spinal cord injury pain, Parkinson's disease related pain, painful epileptic attacks, post stroke pain, deafferentation pain, trigeminal neuralgia, glossopharyngeal neuralgia, thalamic pain, borreliosis pain, phantom pain, and painful restless legs syndrome.

5. The method of claim 3, wherein the peripheral neuropathic pain is selected from the group consisting of brachialgia paraesthetica, carpal tunnel syndrome, erythromelalgia, facial neuralgia, postherpetic neuralgia, postoperative neuralgia, posttraumatic neuralgia, sciatica, causalgia, mononeuropathy, nerve entrapment syndromes, nerve injuries, neuritis pain, occipital neuralgia, trigeminal neuropathy, allodynia and hyperalgesia, sulcus ulnaris syndrome, tarsal tunnel syndrome, radiculopathy, Fabry disease related pain, polyneuropathy, posttraumatic neuropathy, postamputation pain, stump pain and notalgia paraesthetica.

6. The method of claim 3, wherein the nociceptive pain is selected from the group consisting of visceral pain, ischemic pain, Raynaud syndrome related pain, degenerative joint pain such as ost matic pain, tendinitis associated pain, such llodynia, fasciitis pain, keel spur pain, frozen shoulder, arthritis, degenerative vertebral pain, degenerative cervical pain, inflammatory pain, myofascial pain syndrome, muscular trigger points and myalgia.

7. The method of claim 3, wherein the mixed pain syndrome is selected from the group consisting of cervical syndrome, cancer pain, low back pain, abdominal pain, complex regional pain syndrome, postamputation pain, anal pain, disc herniation and degeneration, degenerative spinal pain, failed back surgery syndrome and acute and chronic postsurgical pain.

8. The method of claim 3, wherein the dysfunctional pain is selected from the group consisting of soft tissue rheumatism, fibromyalgia, chronic pelvic pain syndrome, chronic cystitis pain, chronic prostatitis pain, coccygodynia, irritable bowel syndrome, chronic pain of the gut, orofacial pain, proctodynia, vulvodynia, Dercum's disease related pain, widespread pain and craniomandibular dysfunction.

9. The method of claim 1, wherein the headache is selected from the group consisting of cluster headache, migraine, tension type headache, hemicrania, trigeminal autonomic cephalalgia, SUNCT syndrome, nummular headache, occipital neuralgia and trigeminal neuralgia and neuropathy.

10. The method of claim 9, wherein the effective amount of sialyllactose is administered orally, subcutaneously or intravenously.

11. The method of claim 10, wherein the effective amount of sialyllactose achieves a steady-state plasma concentration of between 0.01 and 100 micrograms/mL.

12. The method of claim 10, wherein the effective amount of sialyllactose achieves a steady-state plasma concentration of between 0.1 and 100 micrograms/mL.

13. The method of claim 10, wherein the effective amount of sialyllactose achieves a steady-state plasma concentration of between 0.1 and 75 micrograms/mL.

14. The method of claim 1, wherein the contraindication for is selected from gastrointestinal intolerance, liver impairment or renal impairment.

15. The method of claim 1, wherein the patient is contraindicated for NSAIDs due to hypertension, cardiovascular disease, ulcers, a platelet disorders, impending surgery, concomitant anti-clotting medications, concomitant cyclosporin, fluid retention, kidney disease, liver function impairment, a history of urticaria, pregnancy or breastfeeding.

16. A method of treating inflammatory pain in a patient diagnosed with osteoarthritis and contraindicated for NSAIDs, comprising administering to said patient an effective amount of a sialyllactose wherein the patient experiences an improvement in pain severity and psychometric parameters.

17. The method of claim 16, wherein the sialyllactose compound is a compound selected from a compound of Formula I, I (a) and/or II:

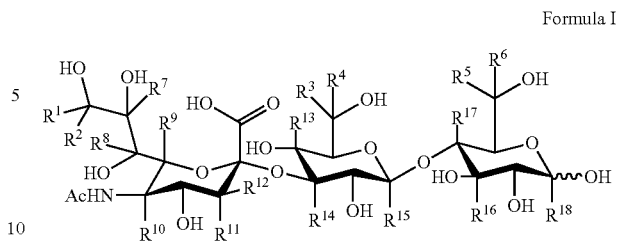
Formula I

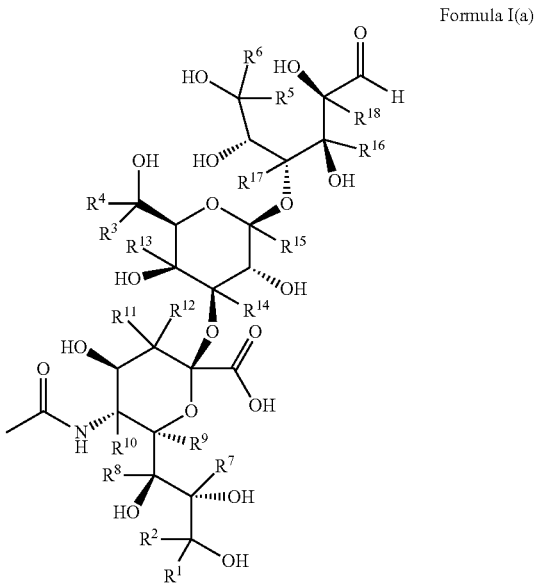
Formula I(a)

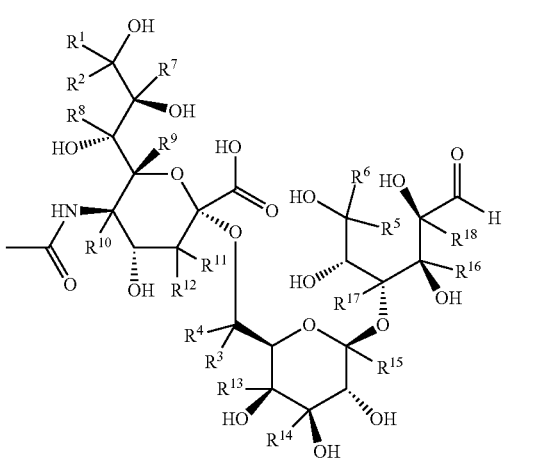
Formula II or a pharmaceutically acceptable salt, solvate, or prodrug thereof, wherein, $R^1$-$R^{18}$ are independently selected from H, D, a halo, an unsubstituted or substituted $C_1$-$C_6$ alkyl, an unsubstituted or substituted $C_1$-$C_6$ heteroalkyl, an unsubstituted or substituted $C_2$-$C_6$ alkenyl, an unsubstituted or substituted $C_2$-$C_6$ heteroalkenyl, an unsubstituted or substituted $C_3$-$C_6$ alkynyl, an unsubstituted or substituted $C_3$-$C_6$ heteroalkynyl, an unsubstituted or substituted $C_4$-$C_8$ cycloalkyl, an unsubstituted or substituted heterocycle, an unsubstituted or substituted aryl, —ROR', —RN(R')$_2$, —RSSR', —SH, —RSOR', —RSO$_2$R', —RSO$_2$H, —RSO$_3$H, —RC(=S)—R', —ROH, —RC(=O) R', —RNO$_2$, —RSR', —RCN, —RNC, —RNNR', —RC(=O) OR', —ROC(=O) R', —RC(=O) H, —RC(=O) OH, —RC(=O)

N(R')$_2$, —RN$_3$, —ROCN, —RNCO, —RONO$_2$, —RNO, —ROP (=O) (OH)$_2$, and —RB (OH)$_2$; R is absent or a (C$_1$-C$_5$) alkyl; and R' is independently selected from H, D, an unsubstituted or substituted C$_1$-C$_6$ alkyl, an unsubstituted or substituted C$_1$-C$_6$ heteroalkyl, an unsubstituted or substituted C$_2$-C$_6$ alkenyl, an unsubstituted or substituted C$_2$-C$_6$ heteroalkenyl, an unsubstituted or substituted C$_3$-C$_6$ alkynyl, an unsubstituted or substituted C$_3$-C$_6$ heteroalkynyl, an unsubstituted or substituted C$_4$-C$_8$ cycloalkyl, an unsubstituted or substituted heterocycle, and an unsubstituted or substituted aryl.

18. The method of claim 16, wherein the patient experiences an improvement in pain severity and/or psychometric parameters.

19. The method of claim 18, wherein the improvement in pain severity and/or psychometric parameters is measured by a patient reported outcome measure selected from the Western Ontario McMaster Osteoarthritis Index, Medical Outcome Studies Short Form 36, Knee Disability and Osteoarthritis Outcome Score, Oxford Knee Score, Disabilities of the Arm, Shoulder and Hand, EUROQOL, Medical Outcomes Study Short Form 12-Item, Hip Disability and Osteoarthritis Outcome Score, Pain Catastrophizing PROM or Oxford Hip Score.

* * * * *